United States Patent
Stern

(10) Patent No.: US 7,637,914 B2
(45) Date of Patent: Dec. 29, 2009

(54) SURGICAL BASE UNIT AND RETRACTOR SUPPORT MECHANISM

(76) Inventor: Leslie Stern, 1030 President Ave., Fall River, MA (US) 02720

( * ) Notice: Subject to any disclaimer, the term of this patent is extended or adjusted under 35 U.S.C. 154(b) by 185 days.

(21) Appl. No.: 11/098,770

(22) Filed: Apr. 4, 2005

(65) Prior Publication Data
US 2006/0036245 A1 Feb. 16, 2006

Related U.S. Application Data

(60) Provisional application No. 60/598,739, filed on Aug. 4, 2004.

(51) Int. Cl.
*A61B 17/60* (2006.01)
(52) U.S. Cl. .................. 606/105; 606/86 R; 606/90; 606/104
(58) Field of Classification Search .............. 606/57, 606/60, 61, 86, 90, 99, 205–208, 86 R, 246, 606/279, 86 A, 999, 104, 105; 600/215, 600/213, 227–231, 234, 235, 210; 294/104; 81/451, 456
See application file for complete search history.

(56) References Cited

U.S. PATENT DOCUMENTS

| | | | | |
|---|---|---|---|---|
| 5,219,349 A | * | 6/1993 | Krag et al. | 606/53 |
| 5,797,963 A | * | 8/1998 | McDevitt | 606/232 |
| 6,126,660 A | * | 10/2000 | Dietz | 606/61 |
| 6,648,888 B1 | * | 11/2003 | Shluzas | 606/61 |
| 6,749,613 B1 | * | 6/2004 | Conchy et al. | 606/61 |
| 7,160,300 B2 | * | 1/2007 | Jackson | 606/273 |
| 2003/0167059 A1 | * | 9/2003 | Young | 606/61 |
| 2003/0187436 A1 | * | 10/2003 | Bolger et al. | 606/61 |
| 2004/0039384 A1 | | 2/2004 | Boehm, Jr. et al. | |

(Continued)

FOREIGN PATENT DOCUMENTS

WO WO 00/48523 8/2000

(Continued)

OTHER PUBLICATIONS

Website: Spinal Concepts-Path Finder™; http://www.spinalconcepts.com/products/pathfinder.htm.

(Continued)

*Primary Examiner*—Eduardo C Robert
*Assistant Examiner*—Tara R George
(74) *Attorney, Agent, or Firm*—Sunstein Kann Murphy & Timbers LLP

(57) ABSTRACT

A method and apparatus for exerting force on a first bone with respect to a fulcrum, which may be a second bone. A pedicle screw with a central threaded socket is inserted into the first bone, and a threaded closure top is driven into the central threaded socket of the pedicle screw. A base structure, mechanically coupled to the fulcrum, is coupled to the closure top so that a force may be exerted by the base structure, acting against the fulcrum, in at least one of axial and transverse directions with respect to the pedicle screw. Coupling between the base structure and the pedicle screw may be by means on an integral assembly that allows both vertical and horizontal forces to be exerted on the bone. The base structure may also support a retractor in a manner local to the immediate region of surgery.

7 Claims, 9 Drawing Sheets

U.S. PATENT DOCUMENTS

| | | | |
|---|---|---|---|
| 2004/0138662 A1* | 7/2004 | Landry et al. | 606/61 |
| 2005/0021040 A1* | 1/2005 | Bertagnoli | 606/90 |
| 2005/0059972 A1* | 3/2005 | Biscup | 606/73 |
| 2005/0085813 A1 | 4/2005 | Spitler et al. | |
| 2005/0216000 A1 | 9/2005 | Colleran et al. | |
| 2005/0245928 A1* | 11/2005 | Colleran et al. | 606/61 |
| 2006/0036240 A1 | 2/2006 | Colleran et al. | |
| 2006/0036244 A1 | 2/2006 | Spitler et al. | |
| 2006/0079894 A1 | 4/2006 | Colleran et al. | |
| 2006/0106380 A1 | 5/2006 | Colleran et al. | |
| 2006/0106394 A1 | 5/2006 | Colleran | |
| 2006/0173454 A1 | 8/2006 | Spitler et al. | |

FOREIGN PATENT DOCUMENTS

| | | |
|---|---|---|
| WO | WO 03/024344 | 3/2003 |
| WO | WO 2004/047650 | 6/2004 |

OTHER PUBLICATIONS

Website: Spine-Health.com; http://www.spine-health.com/topics/surg/mini/mimimally-invasive02.html.; pp. 1-2.

* cited by examiner

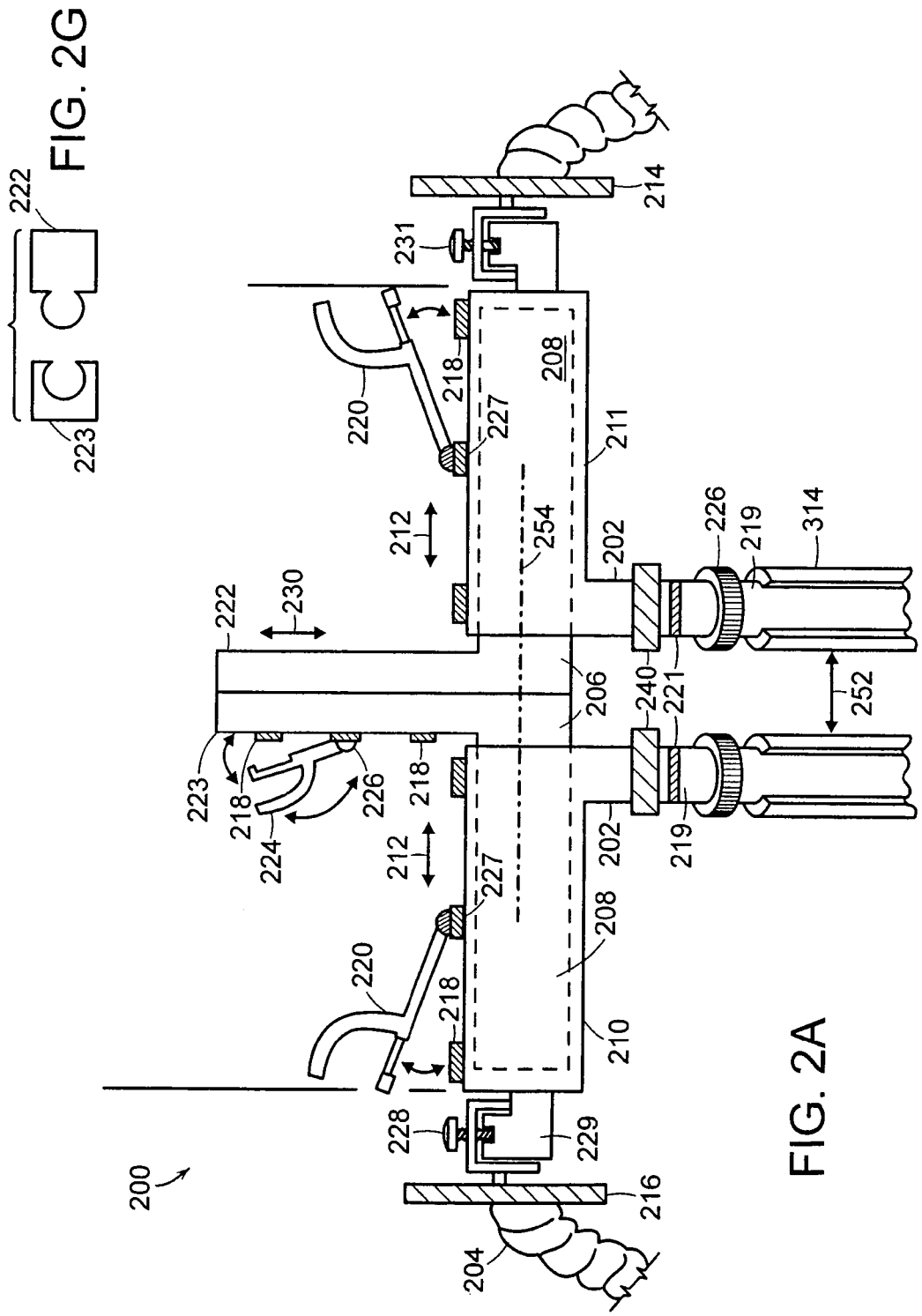

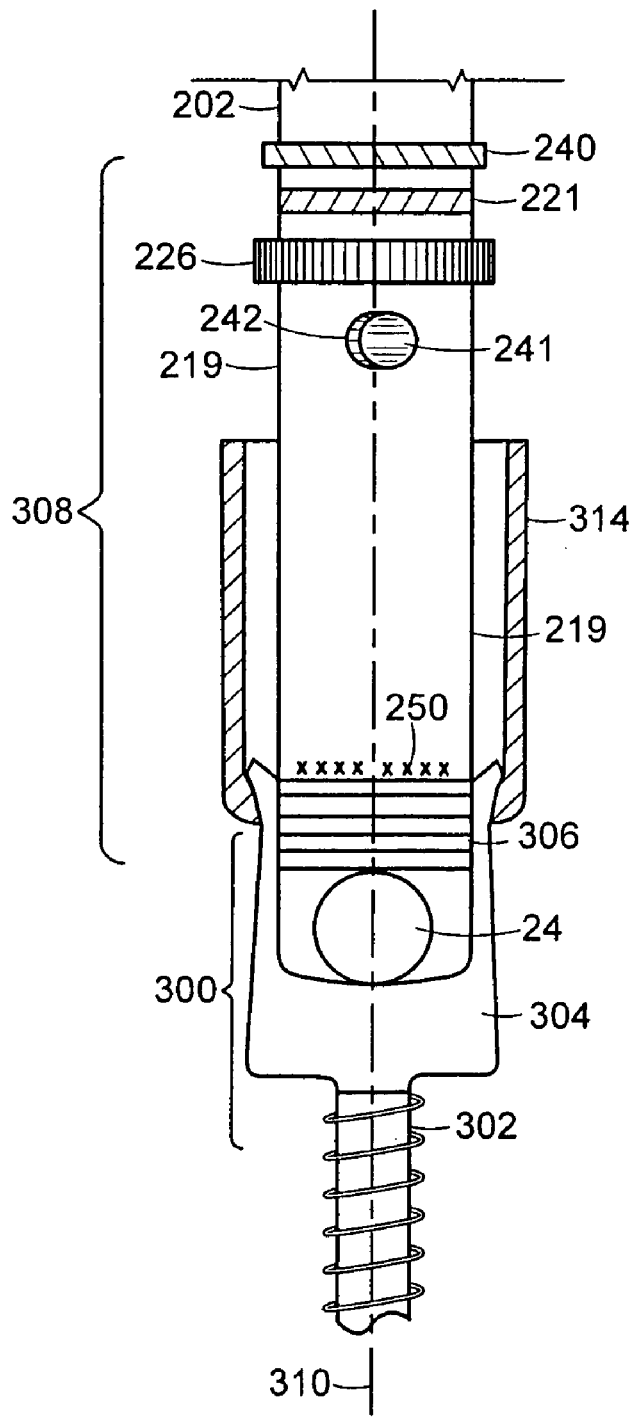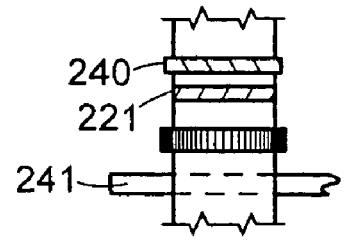
FIG. 3C
FIG. 3A

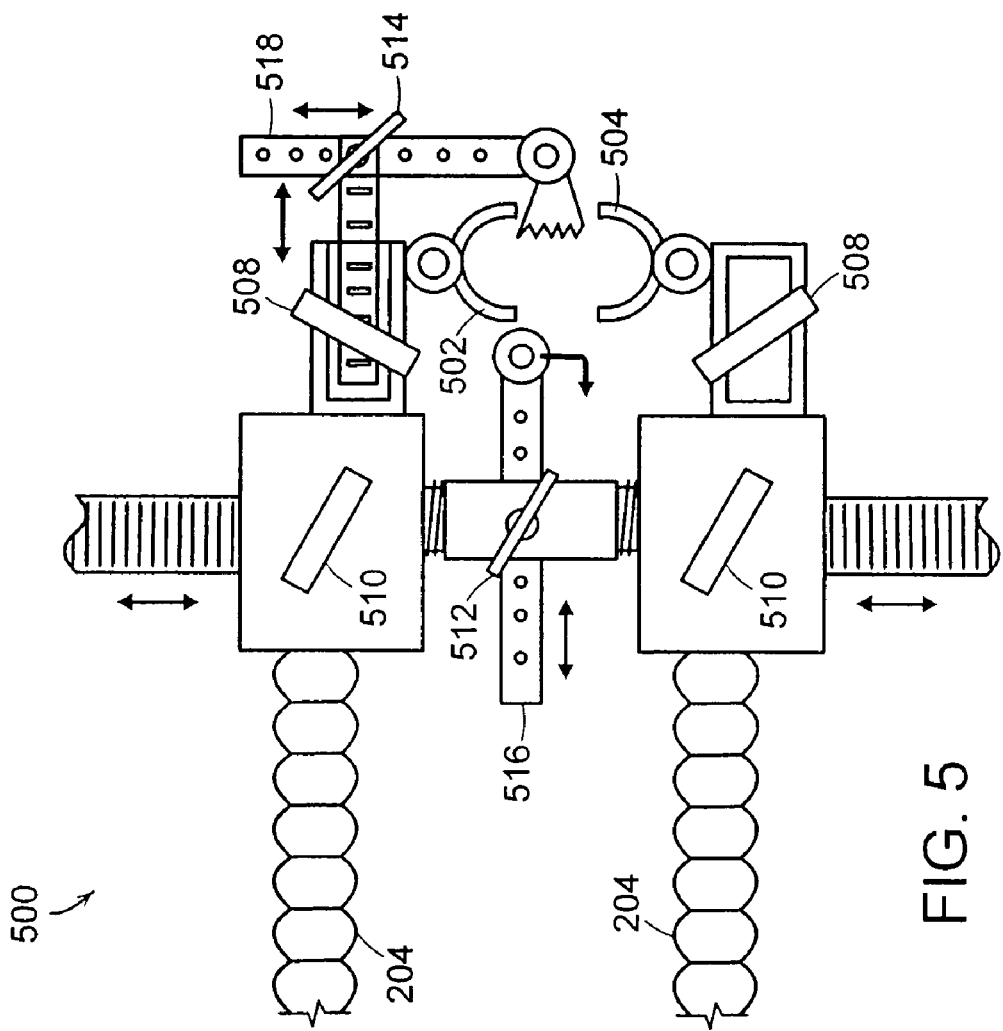

SURGICAL BASE UNIT AND RETRACTOR SUPPORT MECHANISM

The present application claims priority from pending U.S. Provisional Application Ser. No. 60/598,739, filed Aug. 4, 2004, which is incorporated herein by reference.

TECHNICAL FIELD

The present invention pertains to devices and methods for locally securing a support base at the site of an incision by anchoring to a pedicle screw inserted into one or more bones, which support base may be used for exerting relative forces on the bones as well as for supporting a further surgical retractor.

BACKGROUND ART

Fusion of lumbar vertebrae is performed under circumstances including those in which degenerative disk disease, scoliosis, or other deformity indicates that stopping motion between adjacent vertebral segments is desirable. The fusion procedure entails inserting a bone graft between vertebral elements thereby inducing bone growth that ultimately fuses the adjoining vertebral elements. In order to accomplish the fusion of lumbar vertebrae in a minimally invasive manner, procedures, such as those performed in accordance with the Pathfinder™ System of Abbott Spine of Austin, Tex., provide for insertion and retention of a stabilizing rod between pedicle screws, one of which is anchored into each of the adjoining vertebrae, so as to maintain them at a fixed relative displacement after the graft has been inserted and until the biological response completes the fusion process.

It should be noted that lumbar fusion surgery may require relative positioning of adjacent vertebrae in various planes, whether by relative distraction or compression of the intervertebral space, or by reduction, i.e., displacement of a vertebra in a plane transverse to the axis of the spine, i.e., in a direction that will be referred to herein as 'vertical,' as referred to a prone patient.

Using minimally invasive surgical procedures, lumbar fusion surgery is begun as now described with reference to FIG. 1. A first incision 10 is performed in the patient's back 12, parallel to the spine 14 and to one side. Though this incision, pedicle screws 16 and 18 are inserted, by known procedures, into the pedicles of adjoining vertebrae 20 and 22, such as lumbar vertebrae L4 and L5. Rod 24 is inserted through slotted guides in each of pedicle screws 16 and 18 and secured with respect to each of the pedicle screws by closure tops that are threaded for retention in a corresponding helical thread of the pedicle screws. The rest of the procedure proceeds via a second incision 26 made parallel to the first incision 10 and laterally opposite to the first incision on the other side of the spine. Edges of the second incision are held apart by a retractor 28 so that a graft 30 may be inserted between vertebrae 20 and 22. Retractor 28 is typically tethered, via flexible arm 32, to a mounting 34 fixed with respect to the operating table. This method of mounting retractor 28 is unwieldy and not as convenient for the surgeon's unfettered access to the surgical site as might be desired.

It is desirable for reasons both of convenience and sterility that a method and apparatus be provided whereby forces may be applied to a bone, such as a vertebra, with respect to a local fulcrum, and also that a method and apparatus be provided for supporting a retractor 28 locally to the region of the surgery.

SUMMARY OF THE INVENTION

In accordance with preferred embodiments of the present invention, a method is provided for exerting force on a first bone with respect to a fulcrum. The method has steps of inserting a pedicle screw with a central threaded socket into the first bone, and then driving a threaded closure top into the central threaded socket of the pedicle screw. A base structure which is mechanically coupled to the fulcrum is engaged with the closure top so that a force may be exerted by acting against the fulcrum in a direction that is either axial or transverse with respect to the pedicle screw. The direction that is axial with respect to the pedicle screw may also be referred to, herein, as a 'vertical' direction, taken with respect to a prone patient.

In accordance with other embodiments of the invention, the step of engaging the base structure to the closure top may include coupling a leg of the base structure to the closure top. The step of driving the threaded closure top may include driving the closure top by means of a leg extension of the base structure, and the leg extension and closure top may, together, form an integral unit. In an alternate embodiment, the step of driving the closure top may include driving an extended shank of the closure top. A second bone may serve as the fulcrum.

In accordance with other aspects of the invention, a method is provided for securing a retractor to a bone. This method has steps of:
 a. inserting a pedicle screw into the bone, the pedicle screw having a central threaded socket;
 b. driving a threaded closure top into the central threaded socket of the pedicle screw;
 c. engaging a base structure the closure top; and
 d. supporting a retractor from the base structure.

Other embodiments of the invention relate to an apparatus for exerting force on a bone with respect to a fulcrum. The apparatus, in accordance with those embodiments, has a base structure, mechanically coupled to the fulcrum and a leg extension coupled to the base structure, adapted for coupling to a pedicle screw inserted into the bone. Moreover, the apparatus has a simple machine for urging the leg extension in at least one of axial and transverse directions with respect to the pedicle screw by means of the base structure acting against the fulcrum. The simple machine may be a toothed ratchet drive, or a worm drive, and the leg extension may include a threaded end for insertion into a central threaded socket of the pedicle screw. The leg extension may also be rotatably coupled to the base structure, and frangibly coupled to the threaded end.

In accordance with yet further embodiments of the invention, a retractor is provided as a support for non-invasive spinal surgery. The retractor has an adjustable trestle having a cross-bar characterized by a length and two legs coupled to the cross-bar, each leg having an inner cavity for coupling to screws fixed in relation to bone tissue. The adjustable trestle may have one or more telescoping cross-bar sections and a mechanism, that may be a screw mechanism, for adjusting the length of the cross-bar.

Other embodiments of the invention provide a leg assembly for supporting a surgical retractor, wherein the closure top has both a threaded base for retention by a threaded socket in a pedicle screw and an extension coaxial with, and coupled to, the threaded base, adapted to be rotatably coupled to a retractor support. The leg assembly may further include a frangible coupling between the threaded base and the extension.

BRIEF DESCRIPTION OF THE DRAWINGS

The foregoing features of the invention will be more readily understood by reference to the following detailed description, taken with reference to the accompanying drawings, in which:

FIG. 2A shows a support base unit including a support trestle and abutting L segments for applying both axial and vertical forces between pedicle screws anchored in adjoining vertebrae in accordance with preferred embodiments of the present invention;

FIG. 2G is a top view of the upright portions of the base unit, showing their interlocking groove structure, in accordance with certain embodiments of the present invention;

FIG. 3A is a cross section of an elongated closure top supporting a retractor leg in relation to a pedicle screw in accordance with preferred embodiments of the present invention;

FIG. 3C shows the insertion of a torque pin into retractor leg extension of FIG. 3A;

FIG. 5 is a top view of a retractor for minimally invasive surgery as coupled to the base unit of FIG. 2 in accordance with an embodiment of the present invention.

DETAILED DESCRIPTION OF SPECIFIC EMBODIMENTS OF THE INVENTION

Figure 1:
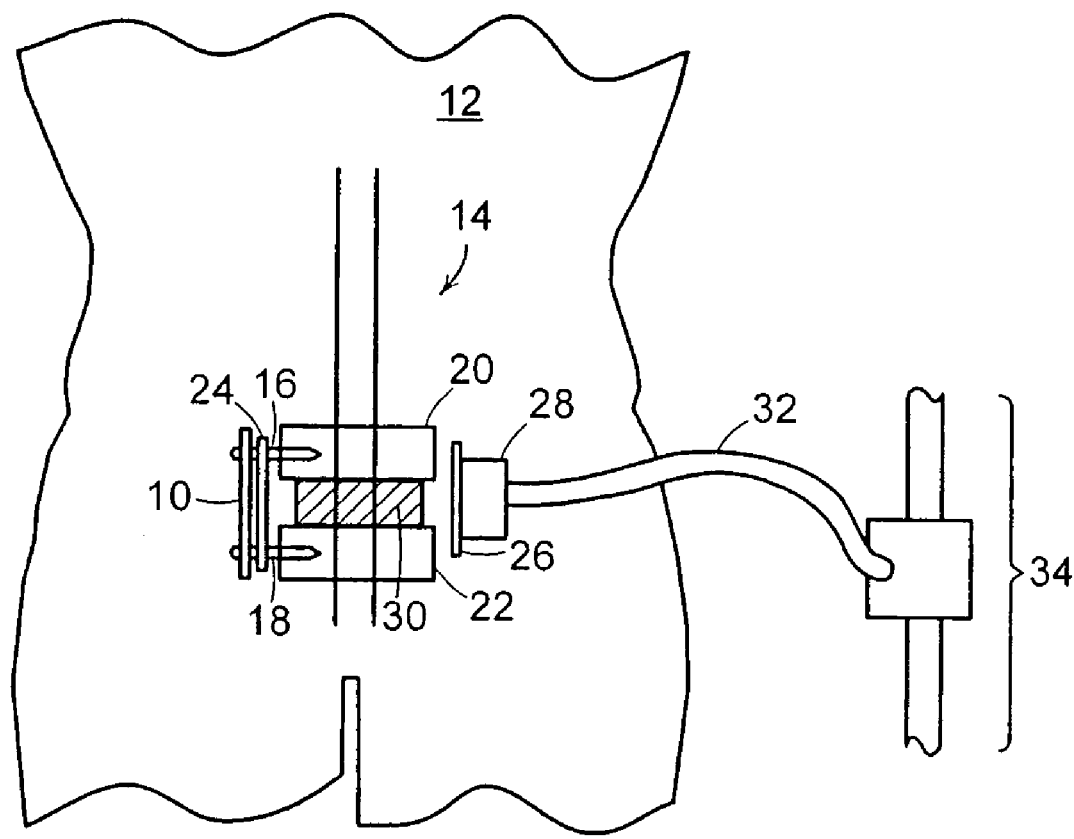
FIG. 1 depicts fundamental features of lumbar fusion surgery in accordance with prior art methods showing a retractor fixed to the operating table.

In accordance with preferred embodiments of the present invention, forces may be applied to a bone with respect to an effectively fixed fulcrum, or between adjacent bones, by a trestle-structure base unit designated generally by numeral 200, as now described with reference to FIG. 2A. Base unit 200 may function alone, or in conjunction with a retractor 500 (shown in FIG. 5) supported by the base unit.

Base unit 200 has two legs (or "posts") 202, each of which is coupled, as described in further detail below, to a pedicle screw 16, 18, anchored to the skeletal system of the patient. Trestle base unit 200 may also serve to support one or more flexible arms 204 to which, in turn, the retractor 500 of FIG. 5 is coupled.

Support of legs 202 of base unit 200 with respect to the pedicle screws is described, now, with reference to FIG. 3A, in which a pedicle screw is designated generally by numeral 300. The application of forces between the components of the base unit will be described below. Pedicle screw 300 is retained within pedicle tissue by means of threads 302 at the distal end of the screw. A pedicle screw 300 may be retained, for example, in the sacrum, in cases where the L5 vertebral body has "slipped" with respect to the sacrum. Pedicle screw body 304 is notched to receive a rod 24, seen here from the end, with the axis of rod 24 directed into the plane of the page. Rod 24, once secured with respect to two pedicle screws, maintains a fixed separation between adjoining vertebrae so that a graft may be inserted between them, and, further, stabilizes the vertebrae until the graft has resulted in fusion of the two vertebrae. Rod 24 is secured with respect to pedicle screw 300 by advancing threaded end 306 of closure top 308 into the correspondingly threaded central socket of pedicle screw body 304.

In the embodiment of the invention depicted in FIG. 3A, closure top assembly 308 is an integral assembly with retractor leg extension 219, the combination comprising a disposable element of the apparatus, and forces may be applied by base unit 200 to a bone, via pedicle screw 304, as described below. After the surgical procedure has been completed, retractor leg extension 219 may be sheared off from closure top neck 306 at breakpoint 250. Alternately, closure top assembly 308 may be withdrawn after the procedure has been completed, and may be replaced with a standard closure top in order to retain rod 24.

Closure top 308 is advanced into pedicle screw body 304 by applying a torque to closure top 308 about central axis 310. In one embodiment of the invention, torque may be applied to closure top 308 by means of a torque pin (or "torque wrench") 241, inserted into through-hole 242, as shown, in its inserted position, in FIG. 3C, or by means of knurled grip 226. In the former embodiment, torque pin 241 facilitates the rotation of retractor leg extension 219 about its axis at radial joint 240, as further discussed below. A front view of the pedicle screw/retractor leg extension assembly is depicted in FIG. 3D.

Figure 3B:
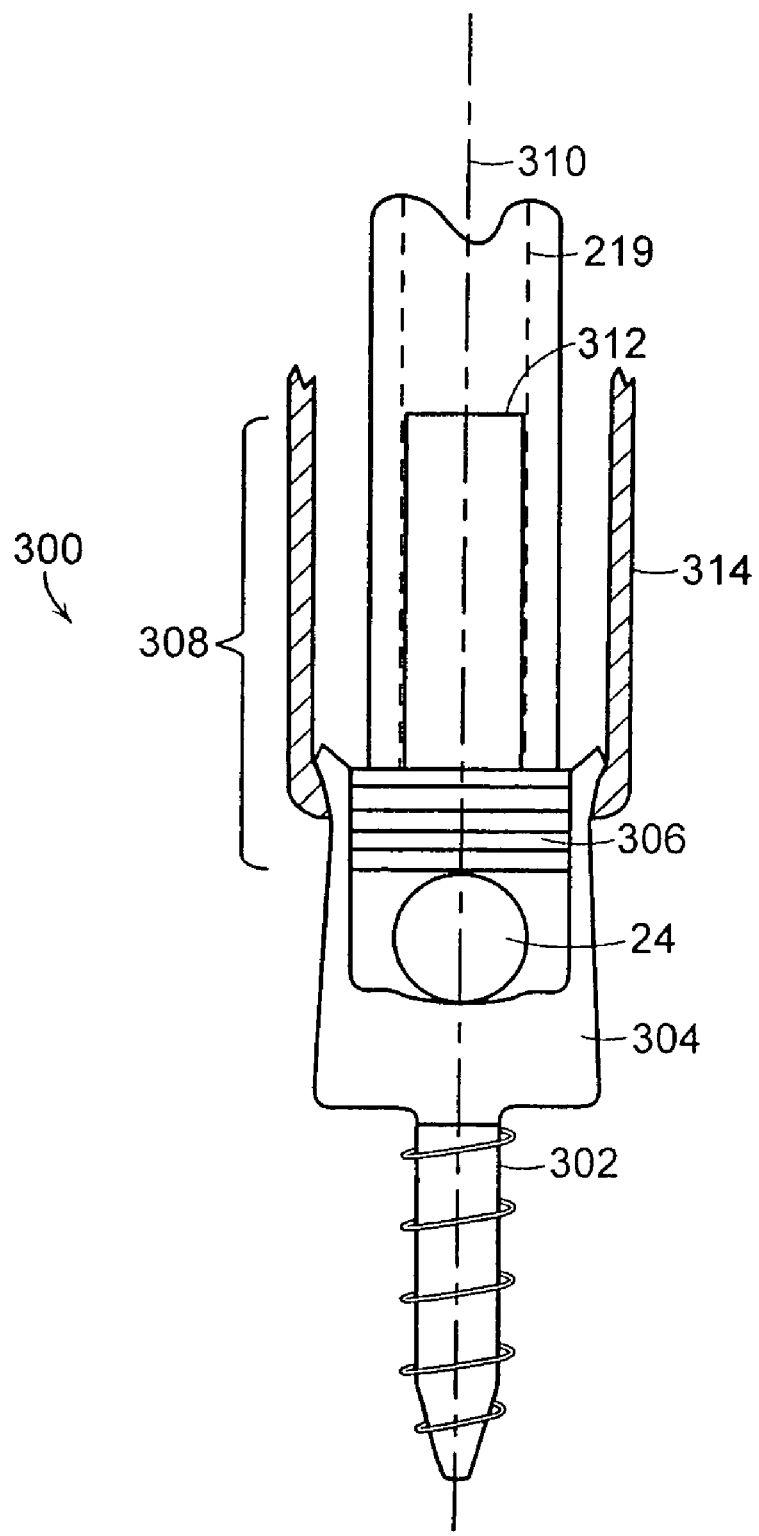
FIG. 3B is a cross section of the elongated closure top of FIG. 3A, through a different rotation angle of the closure top about its longitudinal axis. so as to show the extended shank of the closure top in accordance with preferred embodiments of the present invention.
Figure 3D:
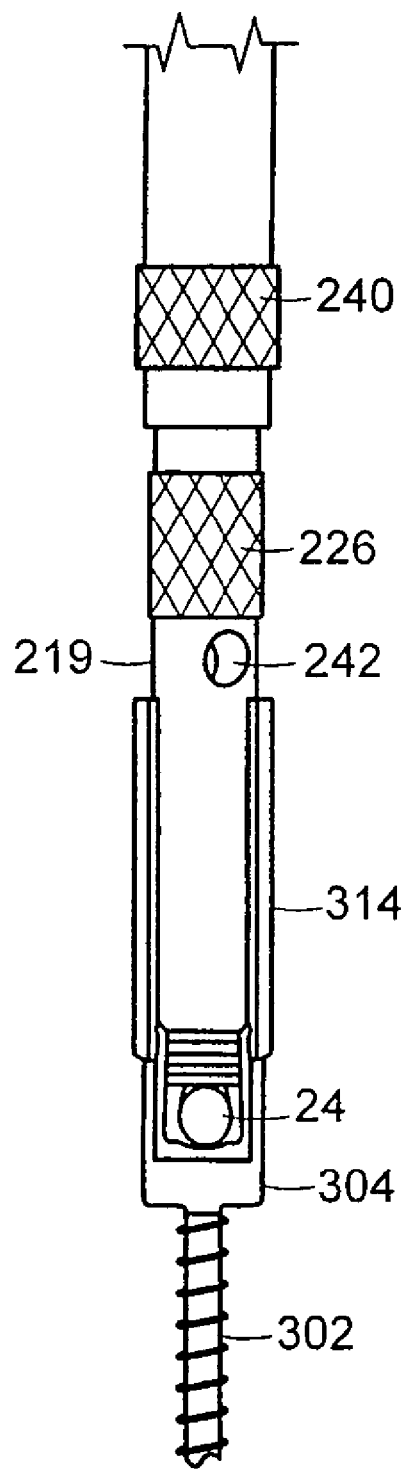
FIG. 3D is a front view of the pedicle screw/retractor leg assembly.

In an entirely different embodiment of the invention, torque is applied to closure top 308 by means of an extended shank 312 that is shown in FIG. 3B. In this alternate embodiment, a tool (such as a socket wrench, or retractor leg extension 219 that has an internal cavity of cross section matching the cross section of the extended shank) captures shank 312, which is the extension of closure top 308. Shank 312, in this case, is characterized by a cross section preferably shaped to facilitate application of torque to the closure top, thus the cross section may be that of a regular polygon, such as a pentagon or hexagon. It is to be understood that the invention is not limited with respect to the means provided for applying torque to drive closure top 308 into pedicle screw 300. For example, shank 312 may also have an interior slot by means of which it is driven with a tool into pedicle screw 300.

In accordance with alternate embodiments of the present invention such as the embodiment depicted in FIG. 3B, extended shank 312 of closure top 308 serves not only for advancing the closure top so as to secure rod 24 but also as a base on which to support leg 202 (or, in yet other embodiments of the invention, an extension 219 thereof) of retractor support structure 200 (shown in FIG. 2). Leg extension 219 is tubular, containing an interior cavity inserted over, and thereby engaged with, shank 312. The cross section of the interior cavity of leg extension 219 may be shaped to mate with the exterior cross section of shank 312. Alternatively, while not a favored embodiment of the invention, it is to be understood that the cross section of interior cavity may also circumscribe the exterior cross section of shank 312 so that the orientation of retractor support structure 200 is not constrained with respect to rotation about axis 310. Leg extension 219, in that embodiment, is inserted over shank 312 and within an extender sleeve 314 of pedicle screw 300, however a separate socket wrench would then typically be used to urge closure top 308 into pedicle screw 300.

Returning now to description of the embodiment depicted in FIG. 3A, leg extension 219 is coupled to support leg 202 by rotational coupling 240 that provides for rotation of leg extension 219 about its longitudinal axis, so that it may be rotated about axis 310, thereby providing torque to closure top 308 for insertion into pedicle screw 300.

Support of legs 202 of retractor support structure 200 by means of closure tops 308 having been described, retractor support 200 is now further described with reference to FIG. 2A. Legs 202 of retractor support 200 are traversed by a cross-bar, designated generally by numeral 206. In accordance with preferred embodiments of the invention, cross-bar 206 has a left sleeve section 210 and a right sleeve section 211, capable of telescoping adjustment with respect to one another so that the length 200 of cross-bar 206 may be adjusted along direction 212 so as to obtain a desired spacing 252 between legs 202 to match the spacing between centers of pedicle screws 300 after attachment to adjacent vertebrae. Adjustment of the length of cross-bar 206 may use any convenient mechanism known in the art. Ratchet handles 220 are used to actuate ratchet mechanisms 227, acting to provide sequential separation of cross-bar sleeve sections 210 and 211 by urging each with respect to inner sections 208, and thereby providing distraction or compression of the bones retaining the pedicle screws to which support legs 202 are attached. Ratchet mechanisms 227 may include a toothed ratchet drive that engages teeth in the inner sections 208. Ratchet levers 220 are locked to pedestals 218 for securing sleeve sections 210 and 211 at a determined relative disposition, once set by adjustment of ratchet mechanisms 227. Other means known in the mechanical arts for adjusting the separation of sleeve sections 210 and 211 (such as a worm drive, for example), and of securing them at a determined relative disposition, are similarly within the scope of the present invention.

In the embodiment of the invention depicted in FIG. 2A, inner transverse sections 208 are the horizontal legs of L-shaped members of which uprights 222 and 223 form the corresponding vertical legs. Uprights 222 and 223 preferably slide with respect to one another while retained in relative alignment by means of the tongue-in-groove configuration shown in the top view of FIG. 2G. Thus, the uprights 222 and 223 may be separated for sterilization purposes. Ratchet mechanism 227, activated by lever 224, acts to urge uprights 222 and 223 in relative vertical displacement, thereby exerting vertical forces, through legs 202, leg extensions 219, and pedicle screws 300, to reduce misalignment in the vertical plane of the bones to which the pedicle screws are attached. For example, misalignment of the spine (listhesis) may be reduced by elevation of a vertebra (typically L5) with respect to the sacrum as a fulcrum.

Figure 2B:
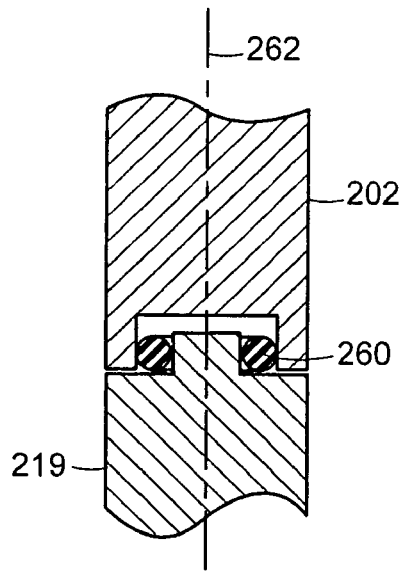
FIGS. 2B-2D show alternate embodiments of the coupling between the support leg of the support base unit and a rotatable leg extension, in accordance with representative embodiments of the present invention.

Sleeve sections 210 and 211 are coupled to legs 202 as further described below with reference to FIG. 5. In preferred embodiments of the invention, leg 202 is coupled to leg extension 219 (which, in preferred embodiments, is part of an integral assembly 308 that includes the closure top) at a snap-lock joint 221. Above the snap-lock joint 221, leg 202 has a rotating coupling 240. One embodiment of rotating coupling 240 is depicted in FIG. 2B where the outer ring of bearing 260 is affixed to retractor leg 202, while the inner ring receives leg extension 219, such that leg extension 219 is free to rotate 360° about longitudinal axis 262.

Figure 2C:
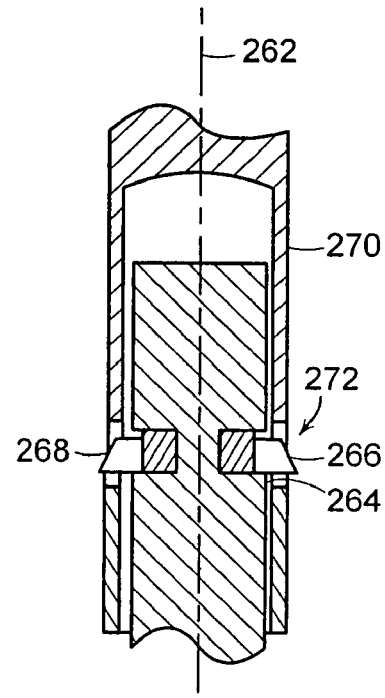
Figure 2D:
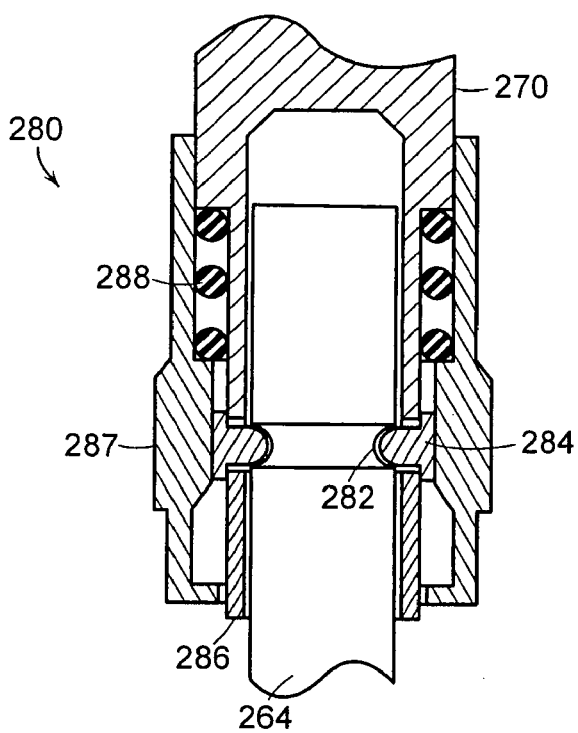
Figures 2E, 2F:
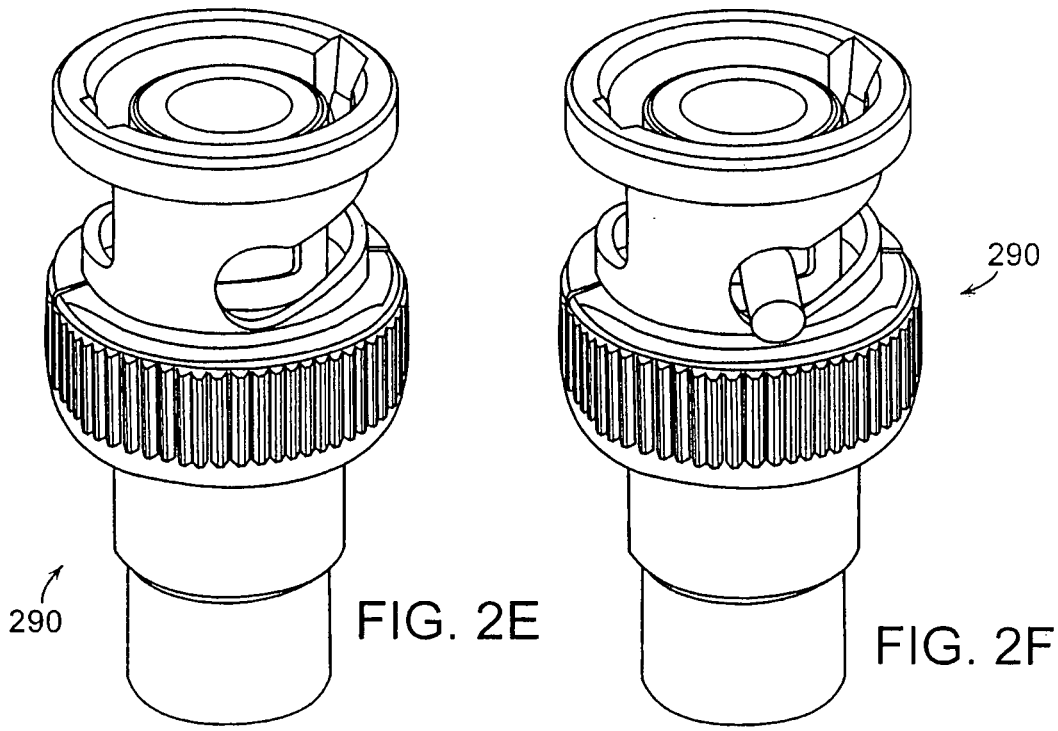
FIGS. 2E and 2F show two views of a twist-and-lock mechanism for coupling the rotatable leg extension to the closure screw, in accordance with certain embodiments of the present invention.
Figure 2H:
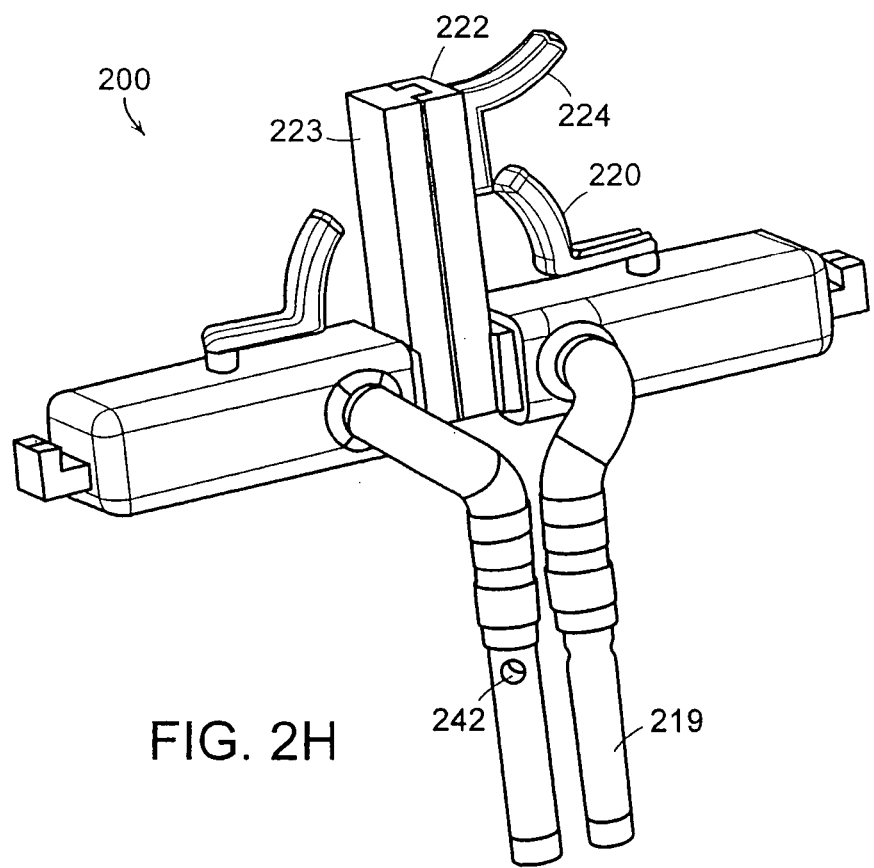
FIG. 2H is a perspective view of the base unit of FIG. 2A.

An exemplary frangible mechanism for engaging an upper leg 270 to a lower leg 264 is shown in FIG. 2C, where lower end 264 of the retractor leg (the lower end may be leg extension 219) contains two locking dogs 266, disposed 180° apart about axis 262, and having angled ends 268. The upper end 270 of retractor leg 202 has two opposed retaining slots 272 for receiving locking dogs 266 of the lower end 264. Locking dogs 266 are biased, by springs, for example, to engage slots 272 thereby maintaining contact between the upper and lower leg segments until the dogs are manually pushed out of retaining slots 272. Another exemplary mechanism for engaging upper leg 270 to lower leg 264 is the representative quick disconnect depicted in FIG. 2D and designated generally by numeral 280. Here, lower leg 264 contains a radial cut 282 that receives dogs 284 coupled to upper leg 270 when sleeve 286 is forced over the dogs by insertion of lower leg 264 into upper leg 270 forcing outer sleeve 287 against spring 288. Lower leg 264 is released by pushing outer sleeve 287 back against spring 288, allowing dogs 284 to release radial cut 282 in the lower leg 264. Quick-disconnect 280 may advantageously provide for free rotation of lower leg 264 with respect to upper leg 270. Other coupling modalities, such as the snap lock 290 depicted in FIGS. 2E and 2F are also within the scope of the present invention.

Figure 4:
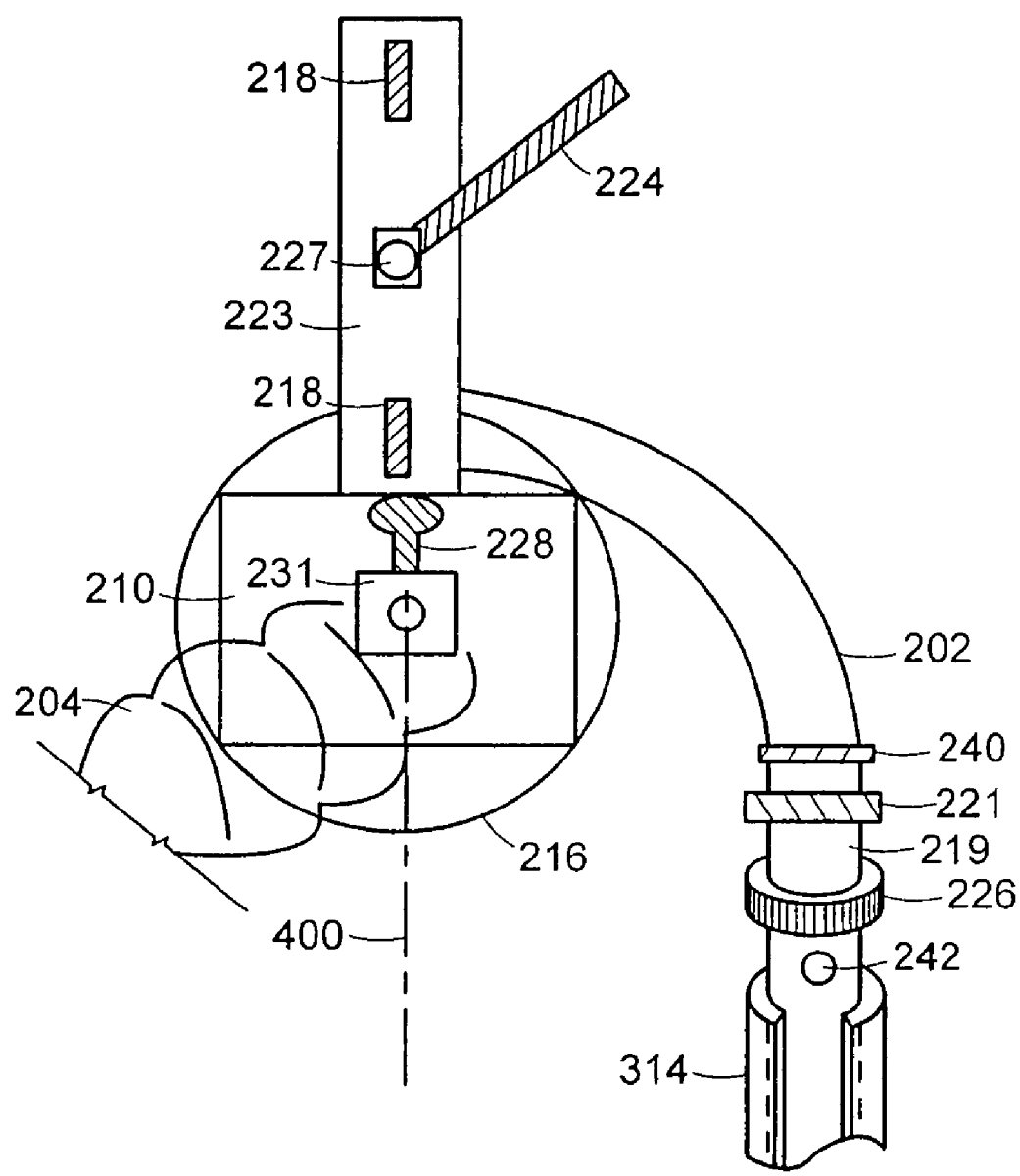
FIG. 4 shows a side view of the support trestle illustrating its coupling to a pedicle screw in accordance with an embodiment of the present invention.

Legs 202 may emanate as right cylinders directly from cross-bar sections 210 and 211, or, in accordance with other embodiments of the invention, may emanate in an arcuate manner, as depicted in FIG. 4 which shows retractor support structure 200 in cross-section as viewed from either the left or right side. While axis 254 (shown in FIG. 2A) of the cross-bar is oriented into the page in FIG. 4, wheel 216 is visible in FIG. 4, as is extender sleeve 314 of pedicle screw 300. The closure top threaded section 306 and extended shank 312 of the closure top are apparent as well. Wheels 214 and 216 are shown, whose purpose is for securing flexible arms 204 which hold each half of the retractor assembly 500, as shown in FIG. 5. Flexible arms 204 are locked to base unit 200 by screws 228 or other connectors.

In accordance with further embodiments of the invention, a flexible arm 204 extends from one or both sides of the retractor support structure and supports retractor 500, one embodiment of which is now described with reference to FIG. 5. Retractor 500 is shown in FIG. 5 as viewed from above. The retractor is supported, at the site of the surgery, by means of flexible arms 204 which couple it rigidly, but adjustably, to the retractor support structure described in the foregoing sections. Retractor 500 serves to retain spreaders 502 and 504 at a spacing prescribed by the surgeon to provide access to the region between vertebrae for excision of a disk or insertion of a graft. In an exemplary embodiment of the invention, the placement of pull pins 512 and 514 with respect to perforated spacing members 516 and 518 respectively, govern the coarse placement of the retractor in two orthogonal directions. Fine lateral adjustments of the position and opening of spreaders 502 and 504 is provided by ratchets 508 and 510.

The retractor support mechanism herein described may advantageously serve for procedures of posterior lumbar interbody fusion (PLIF) and translateral interbody fusion (TLIF). Its applicability, however, is not so limited and it may advantageously be applied in surgical circumstances where local support of a retractor relative to bone is desirable.

Moreover, the described embodiments of the invention are intended to be merely exemplary and numerous variations and modifications will be apparent to those skilled in the art. All such variations and modifications are intended to be within the scope of the present invention as defined in the appended claims.

What is claimed is:

1. A method for exerting force on a first bone with respect to a fulcrum, the method comprising:

a. inserting a pedicle screw into the first bone, the pedicle screw having a central threaded socket;
b. driving a threaded closure top into the central threaded socket of the pedicle screw;
c. engaging a base structure, mechanically coupled to the fulcrum, in direct engagement with the closure top by means of a leg extension; and
d. exerting a differential force on the first bone relative to the fulcrum or a second bone simultaneously in both axial and transverse directions with respect to the pedicle screw, while retaining vertical alignment of an upright member, by means of the base structure acting against the fulcrum.

2. A method in accordance with claim 1, wherein the step of driving the threaded closure top includes driving the closure top by means of said leg extension of the base structure.

3. A method in accordance with claim 1, wherein the step of driving the threaded closure top includes driving an extended shank of the closure top.

4. A method in accordance with claim 1, wherein the second bone serves as the fulcrum.

5. A method in accordance with claim 2, wherein the leg extension and closure top comprise an integral unit.

6. A method for exerting force on a first bone with respect to a fulcrum, the method comprising:
   a. inserting a pedicle screw into the first bone, the pedicle screw having a central threaded socket;
   b. driving a threaded closure top into the central threaded socket of the pedicle screw;
   c. engaging a singular base structure, mechanically coupled to the fulcrum by means of a leg extension, in direct engagement with the closure top; and
   d. exerting a differential force on the first bone relative to the fulcrum or a second bone in both axial and transverse directions with respect to the pedicle screw, while retaining alignment of an upright member, by means of the singular base structure acting against the fulcrum.

7. A method for retaining adjoining vertebrae in reduction during the course of insertion of a bone graft between the adjoining vertebrae, the method comprising:
   a. inserting a first pedicle screw into a first vertebra;
   b. inserting a second pedicle screw into a second vertebra;
   c. engaging a base structure having a plurality of legs, each leg directly coupled to a closure top, in a mechanical coupling with each of the first and second pedicle screws by the closure tops; and
   d. exerting a differential force on the first pedicle screw relative to the second pedicle screw in at least an axial direction with respect to the first pedicle screw by means of a member of the base structure acting against a fulcrum; and
   e. maintaining the first and second vertebrae in simultaneous distraction and reduction, while retaining alignment of upright members, during the course of insertion of the bone graft.

* * * * *

UNITED STATES PATENT AND TRADEMARK OFFICE
CERTIFICATE OF CORRECTION

| | |
|---|---|
| PATENT NO. | : 7,637,914 B2 |
| APPLICATION NO. | : 11/098770 |
| DATED | : December 29, 2009 |
| INVENTOR(S) | : Leslie Stern |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 349 days.

Signed and Sealed this

Ninth Day of November, 2010

David J. Kappos
*Director of the United States Patent and Trademark Office*